(12) United States Patent
Wong et al.

(10) Patent No.: US 10,068,058 B2
(45) Date of Patent: Sep. 4, 2018

(54) METHOD AND APPARATUS FOR IMPROVED CLINICAL SYSTEM PERFORMANCE

(71) Applicant: Change Healthcare Holdings, LLC, Nashville, TN (US)

(72) Inventors: Eldon Wong, Vancouver (CA); Itai Galili, Vancouver (CA); Laurie Bergeron, Ancaster (CA)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 174 days.

(21) Appl. No.: 15/086,155

(22) Filed: Mar. 31, 2016

(65) Prior Publication Data

US 2017/0286605 A1    Oct. 5, 2017

(51) Int. Cl.
| | |
|---|---|
| *G06F 15/177* | (2006.01) |
| *G06F 19/00* | (2018.01) |
| *H04L 12/24* | (2006.01) |
| *G16H 40/20* | (2018.01) |

(52) U.S. Cl.
CPC ........... *G06F 19/327* (2013.01); *G16H 40/20* (2018.01); *H04L 41/082* (2013.01)

(58) Field of Classification Search
CPC .............................. G06F 19/327; H04L 41/082

USPC ........................................................ 709/220
See application file for complete search history.

(56) References Cited

U.S. PATENT DOCUMENTS

| | | | | |
|---|---|---|---|---|
| 2013/0297330 A1* | 11/2013 | Kamen | ................ | G06F 19/323 705/2 |
| 2013/0317753 A1* | 11/2013 | Kamen | ............... | G06F 19/3412 702/19 |
| 2014/0207486 A1* | 7/2014 | Carty | .................... | G06Q 50/22 705/2 |
| 2015/0154364 A1* | 6/2015 | Biasi | ................... | G06F 19/3412 709/223 |

* cited by examiner

*Primary Examiner* — Kristie Shingles
(74) *Attorney, Agent, or Firm* — Alston & Bird LLP (57) ABSTRACT

A method, apparatus and computer program product provide mechanisms for implementing a clinical client monitoring and configuration system. The method includes receiving system data from a plurality of client clinical devices, each of the plurality of client clinical devices implementing a reporting framework for transmission of the system data, determining, based on the system data, at least one clinical client application configuration change for a clinical application executing on at least one of the plurality of client clinical devices or another client clinical device other than the plurality of client clinical devices, and transmitting instructions to the clinical application for implementation of the at least one clinical client application configuration change.

17 Claims, 4 Drawing Sheets

METHOD AND APPARATUS FOR IMPROVED CLINICAL SYSTEM PERFORMANCE

TECHNOLOGICAL FIELD

Example embodiments of the present invention relate generally to methods, systems, and computer readable storage media for providing improved configuration of networked clinical devices and, more particularly, to methods, systems, and computer readable media for providing improved performance and configuration of networked clinical devices through the use of performance analytics.

BACKGROUND

The movement to electronic health records and general proliferation of computer networks has led to a rapid expansion of the use of networked computing devices by healthcare organizations (HCO). A given HCO may use networked computers for storing and accessing patient electronic health records using internal and external records systems, capturing and reviewing medical images, monitoring patient admission statuses, performing insurance and patient billing operations, managing clinician tasks, managing ward bed assignments, and more. Interlinking these systems with one another provides innumerable benefits by ensuring that data is efficiently exchanged and propagated across systems. However, these interdependencies may also introduce issues and challenges when technical problems occur with one or more computing devices of the system.

While tools for monitoring the technical status of computing device exist, these tools lack awareness or knowledge of the complex interrelationships that occur in HCO computer networks. Through applied effort, ingenuity, and innovation, the inventors have solved many of these identified problems by developing a technical solution that is embodied by the present invention, which is described in detail below.

BRIEF SUMMARY

Methods, apparatuses and computer program products are therefore provided according to example embodiments of the present invention in order to provide improved techniques for monitoring the status of clinical applications and taking action to improve the performance of those clinical actions based on reported data. Embodiments provide for the use of a reporting framework to distribute monitoring scripts to client devices executing clinical applications, to execute those monitoring scripts, and to receive system data from those monitoring scripts. Embodiments also provide for receiving clinical data from one or more clinical applications executing on those client devices, and using the received system data and the received clinical data to identify faults and effect configuration changes to one or more of the client devices. Embodiments may thus function to efficiently identify the status of client devices, identify any impact that the status of those devices will have on the clinical applications executing on those devices or using those devices, and take appropriate action to remedy any problems or notify users so that problems can be addressed.

An example of an embodiment includes a method for implementing a clinical client monitoring and configuration system. The method includes receiving system data from a plurality of client clinical devices, each of the plurality of client clinical devices implementing a reporting framework for transmission of the system data, determining, based on the system data, at least one clinical client application configuration change for a clinical application executing on at least one of the plurality of client clinical devices or another client clinical device other than the plurality of client clinical devices, and transmitting instructions to the clinical application for implementation of the at least one clinical client application configuration change.

In some embodiments, the method includes transmitting at least one of a script or executable instructions to the plurality of client clinical devices via the reporting framework, such that execution of the script or executable instructions causes a client clinical device receiving the script or executable instructions to transmit the system data. The system data may include performance data for one or more of the plurality of client clinical devices. Determining the configuration change may include determining, from the system data, that a first viewer application has failed, and routing at least one imaging study from the first viewer application to a second viewer application. The method may include configuring at least one launch configuration file of at least one of the plurality of client clinical devices to use the second viewer application to view the imaging study instead of the first viewer application. The method may include receiving clinical data from the clinical application, wherein the configuration change is determined based in further part on the clinical data. The plurality of client clinical devices may include at least one of a Picture Archiving and Communications System, an electronic health records system, a Health Level 7 (HL7) server, or an admission, discharge, transfer system.

Another example of an embodiment includes an apparatus for implementing a clinical client monitoring and configuration system. The apparatus includes a processor and a memory, the memory storing instructions that are executed by the processor to configure the processor to at least receive system data from a plurality of client clinical devices, each of the plurality of client clinical devices implementing a reporting framework for transmission of the system data, determine, based on the system data, at least one clinical client application configuration change for a clinical application executing on at least one of the plurality of client clinical devices or another client clinical device other than the plurality of client clinical devices, and transmit instructions to the clinical application for implementation of the at least one clinical client application configuration change.

In some embodiments, the apparatus may be further configured to transmit at least one of a script or executable instructions to the plurality of client clinical devices via the reporting framework, such that execution of the script or executable instructions causes a client clinical device receiving the script or executable instructions to transmit the system data. The system data may include performance data for one or more of the plurality of client clinical devices. Determining the configuration change may include determining, from the system data, that a first viewer application has failed, and routing at least one imaging study from the first viewer application to a second viewer application. The apparatus may be further configured to configure at least one launch configuration file of at least one of the plurality of client clinical devices to use the second viewer application to view the imaging study instead of the first viewer application. The apparatus may be further configured to receive clinical data from the clinical application. The configuration change may be determined based in further part on the clinical data. The plurality of client clinical devices may include at least one of a Picture Archiving and Communications System, an electronic health records system, a Health Level 7 (HL7) server, or an admission, discharge, transfer system.

Another example of an embodiment includes a non-transitory computer readable storage medium comprising program instructions that, when executed by a processor, configure the processor to at least receive system data from a plurality of client clinical devices, each of the plurality of client clinical devices implementing a reporting framework for transmission of the system data, determine, based on the system data, at least one clinical client application configuration change for a clinical application executing on at least one of the plurality of client clinical devices or another client clinical device other than the plurality of client clinical devices, and transmit instructions to the clinical application for implementation of the at least one clinical client application configuration change.

In some embodiments, the instructions further configure the processor to transmit at least one of a script or executable instructions to the plurality of client clinical devices via the reporting framework, such that execution of the script or executable instructions causes a client clinical device receiving the script or executable instructions to transmit the system data. The system data may include performance data for one or more of the plurality of client clinical devices. Determining the configuration change may include determining, from the system data, that a first viewer application has failed, and routing at least one imaging study from the first viewer application to a second viewer application. The instructions may further configure the processor to configure at least one launch configuration file of at least one of the plurality of client clinical devices to use the second viewer application to view the imaging study instead of the first viewer application. The instructions may be further configured to receive clinical data from the clinical application, wherein the configuration change is determined based in further part on the clinical data.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having thus described certain embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Introduction

A method, apparatus and computer program product are provided in accordance with example embodiments of the present invention to provide improved monitoring of client clinical devices. As noted above, the inventors have identified that present computer networks are often inadequate for performing common clinical tasks due to interdependencies among system components and the impact of a failure of one or more client clinical devices on the ability of the system to support clinical workflows. Embodiments include the use of a framework to transmit monitoring applications (e.g., scripts) to client clinical devices which report back system data related to those client clinical devices. Embodiments may further receive clinical data from those same client clinical devices to determine the status of clinical applications executing upon those devices from the perspective of the clinical application. Together, the system data and the clinical data may be analyzed by a rule engine component to determine the impact of changes to the status of the client clinical devices on clinical operations being performed by the networked client clinical devices.

For the purposes of this disclosure, the term "client clinical device" refers to any computing device or group of devices acting in concert with one another that executes a clinical application and which is in communication with a clinical application monitoring and configuration server as described herein. It should be appreciated that such client clinical devices may not necessarily be in a client/server relationship with other devices and may act as standalone devices or even as server devices for certain applications. For example, an electronic health records server would be a client clinical device as described herein, assuming the electronic health records server implemented the necessary monitoring component to report system data to a clinical application monitoring and configuration server.

For the purposes of this application, the term "clinical application" should be understood to refer to any application used by a HCO to assist with any element of patient care, including but not limited to accessing patient electronic health records, viewing patient medical studies (e.g., a Picture Archiving and Communications System workstation or a Radiological Information System workstation), transmitting medical messages (e.g., HL7 messages), performing patient billing operations, receiving medical dictations, or the like.

For the purposes of this application, the term "system data" should be understood to refer to data related to the hardware or operating system status of a client clinical device. The system data may include, but is not necessarily limited to, performance characteristics such as processor and memory utilization, available storage, processor operating temperature, network bandwidth utilization, or the like. The system data may also include other status characteristics such as the number and identity of processes executing on the client clinical device, a device identifier, a network adapter medium access control (MAC) or Internet Protocol (IP) address, data relating to a network topology, data related to a system configuration, or the like. It should be appreciated that such system data is generally made available and obtained through direct interactions with device hardware (e.g., via device drivers and application programming interfaces (APIs)) and the device operating system.

For the purposes of this application, the term "clinical data" refers to information received from the one or more clinical applications executing on the client clinical device. For example, clinical data may include information relating to a particular patient being viewed, a medical study that is opened, a status of a clinical application as reported by the clinical application itself, an identity of another computing node or device being accessed by the clinical application (e.g., a server being accessed by a client clinical application or client applications in communication with a server executing a clinical application), data indicating a configuration of a clinical application (e.g., view settings for a medical viewer application or database table data for an electronic health records application) or the like. Clinical data is distinguished from system data by virtue of the fact that clinical data is collected and reported by the clinical application executing on the client clinical device, while the system data is collected and reported by one or more monitoring components in communication with client clinical device hardware or operating system elements.

Exemplary Client and Server Apparatuses

Figure 1:
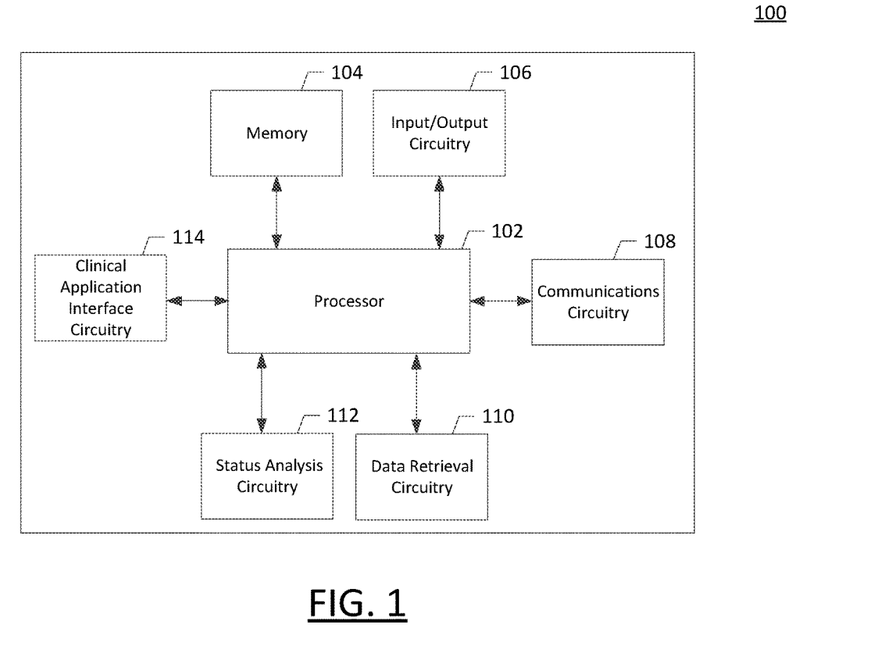
FIG. 1 is a block diagram of an apparatus for providing improved monitoring of client clinical devices in accordance with some embodiments of the present invention.

FIG. 1 illustrates a block diagram of an apparatus 100 in accordance with some example embodiments. The apparatus 100 may be any computing device capable of receiving system data and monitoring the status of a plurality of client clinical devices as described herein. For example, the apparatus 100 may be implemented as a computing device executing one or more applications for receiving data from client clinical devices, processing the received data to determine the impact of the status of the client clinical devices on clinical operations, and effecting configuration changes to those client clinical devices as appropriate.

The apparatus 100 may be implemented as a standalone or rack-mounted server, a desktop computer, a laptop computer, a personal digital assistant, a tablet computer, a netbook computer, a mobile device, or the like. Accordingly, it will be appreciated that the apparatus 100 may comprise devices, hardware, and the like configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

As illustrated in FIG. 1, an apparatus 100 may include a processor 102, a memory 104, input/output circuitry 106, communications circuitry 108, data retrieval circuitry 110, status analysis circuitry 112, and clinical application interface circuitry 114. The apparatus 100 may be configured to manage monitoring and configuration of client clinical devices as described below with respect to FIGS. 3 and 5. Although these components 102-114 are described with respect to functional limitations, it should be understood that the particular implementations necessarily include the use of particular hardware. It should also be understood that certain of these components 102-114 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, "circuitry" includes programmed processing circuitry, storage media, network interfaces, input/output devices, and/or the like. In some embodiments, other elements of the apparatus 100 may provide or supplement the functionality of particular circuitry. For example, the processor 102 may provide processing functionality, the memory 104 may provide storage functionality, the communications circuitry 108 may provide network interface functionality, and the like, such that each of the circuitries may be formed by other circuitry components of the apparatus 100.

In some embodiments, the processor 102 (and/or co-processor or any other processing circuitry assisting or otherwise associated with the processor) may be in communication with the memory 104 via a bus for passing information among components of the apparatus. The memory 104 may be non-transitory and may include, for example, one or more volatile and/or non-volatile memories. In other words, for example, the memory may be an electronic storage device (e.g., a computer readable storage medium). The memory 104 may be configured to store information, data, content, applications, instructions, tables, data structures, or the like, for enabling the apparatus to carry out various functions in accordance with example embodiments of the present invention.

The processor 102 may include various processing devices and may, for example, include one or more processing devices configured to perform independently from one another. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 102 may be configured to execute instructions stored in the memory 104 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, and the instructions may specifically configure the processor to perform the algorithms and/or operations described herein when the instructions are executed.

In some embodiments, the apparatus 100 may include input/output circuitry 106 that may, in turn, be in communication with the processor 102 to provide output to the user and, in some embodiments, to receive an indication of a user input. The input/output circuitry 106 may comprise a user interface and may include a display and may comprise a web user interface, a mobile application, a client device, a kiosk, or the like. In some embodiments, the input/output circuitry 106 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 104, and/or the like). The input/output circuitry 106 may provide a mechanism for display of an improved visualization interface (e.g., via a monitor or other display), and receiving input related to that improved visualization interface (e.g., a mouse, keyboard, or the like).

The communications circuitry 108 may be any means such as a device or circuitry embodied in either hardware or a combination of hardware and software that is configured to receive and/or transmit data from/to a network and/or any other device, circuitry, or module in communication with the apparatus 100. In this regard, the communications circuitry 108 may include, for example, a network interface for enabling communications with a wired or wireless communication network. For example, the communications circuitry 108 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The data retrieval circuitry 110 includes hardware configured to communicate with client clinical devices to retrieve system data. For example, the system data may be retrieved via a framework for capturing and reporting device system data. For example, each client clinical device may implement a local application that communicates with a server for the purpose of capturing dynamically definable analytics, receiving and executing scripts, and the like. The data retrieval circuitry 110 may include hardware for implementing or accessing such a server (e.g., a network interface implemented by the communications circuitry 108) to provide monitoring applications or scripts to the client clinical devices and to obtain system data from those client clinical devices. The data retrieval circuitry 110 may thus implement code that, when executed by the processor 102 or another processing element, causes the processor or processing element to access, retrieve, monitor, or poll a network endpoint, shared memory, or other mechanism for receiving such data. The system data received by the data retrieval circuitry 110 may be provided to the status analysis circuitry 112 via a bus, shared memory, or the like to allow the status analysis circuitry 112 to utilize the system data in analyzing the status of client clinical devices and the impact of that status on clinical operations.

The status analysis circuitry 112 includes hardware configured to process received clinical data and system data and to take appropriate action in response to determining that the received data indicates there will be an impact on clinical operations of one or more client clinical devices coupled to the apparatus 100. To this end, the status analysis circuitry 112 may implement a rules engine which detects the presence of certain status criteria and determines that a given rule is satisfied by the status criteria. For example, the status analysis circuitry 112 may determine that received system data meets or exceeds certain threshold values (e.g., performance data indicating certain performance thresholds are met or exceeded), and/or that clinical data indicates that clinical applications are in certain status conditions. In this manner, the status analysis circuitry 112 is operable to make determinations of proper actions and configuration settings for client clinical devices based not only on data received from the clinical applications, but also based on system data related to the administration of the hardware and operating system constructs of the client clinical devices themselves. To perform these functions, the status analysis circuitry may implement the rules engine via processing circuitry, such as the processor 102, which may be implemented as special-purpose processing circuitry or a programmed general purpose processor.

The status analysis circuitry 112 may generate various forms of output, which may be transmitted to the clinical application interface circuitry 114 via a shared memory, bus, network interface, or other mechanism for instructing the clinical application interface circuitry 114 to take particular actions in support of the clinical functioning of one or more of the client clinical devices.

The clinical application interface circuitry 114 includes hardware configured to communicate with one or more client clinical devices to obtain clinical data reported by clinical applications executing on those client clinical devices and to configure clinical applications executing on those client clinical devices. To this end, the clinical application interface circuitry 114 may include various hardware for communicating data to and from the clinical applications, such as network interface cards, buses, shared memories, or the like. In some embodiments, these communication tasks may be performed by the communications circuitry 108. Processing tasks related to monitoring of clinical applications may be performed by processing elements, such as the processor 102 or the like. The clinical application interface circuitry 114 may implement an interface layer between the status analysis circuitry 112 and the one or more clinical applications.

It should be appreciated that, while the clinical application interface circuitry 114 and the data retrieval circuitry 110 are described in this and other exemplary embodiments as being separate and distinct elements, in some embodiments the associated functionality for each may be implemented by a single hardware or software element having the ability to receive both system data and clinical data and to effect the configuration of clinical applications and to provide monitoring applications or scripts to client clinical devices.

As will be appreciated, any computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Figure 2:
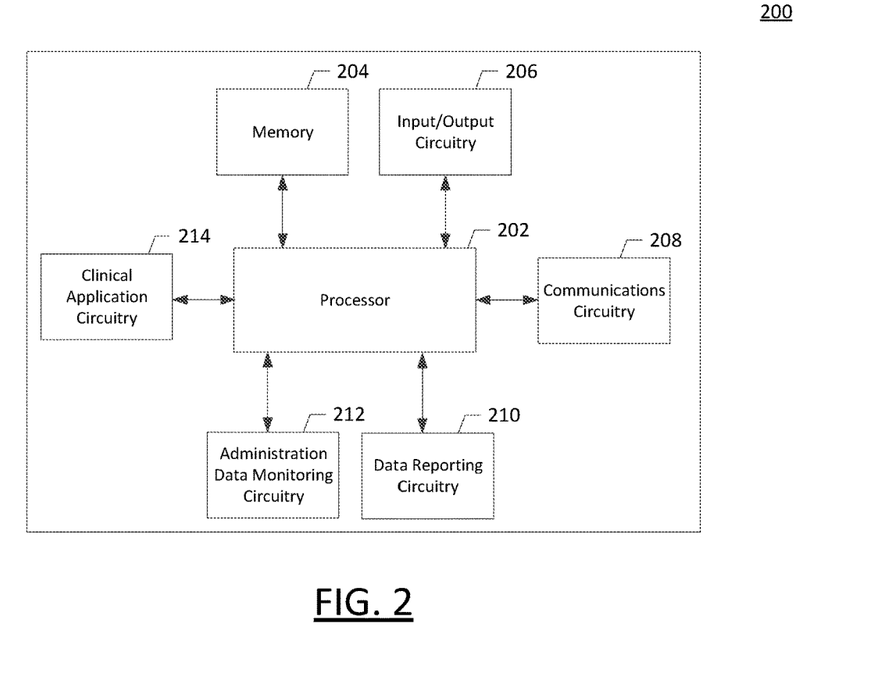
FIG. 2 is a block diagram of an apparatus which may function as a client device executing a clinical application in accordance with some embodiments of the present invention.

FIG. 2 illustrates an apparatus 200 for implementing a client clinical device in accordance with embodiments of the present invention. As described above, a client clinical device is a computing device configured to perform one or more functions in support of a clinical task while also reporting system data to a server, such as the apparatus 100 described above with respect to FIG. 1.

The apparatus 200 includes a processor 202 a memory 204, input/output circuitry 206, communications circuitry 208, data reporting circuitry 210, system data monitoring circuitry 212, and clinical application circuitry 214. The processor 202, memory 204, input/output circuitry 206, and communications circuitry 208 may be implemented in a similar manner as the corresponding components described above with respect to FIG. 1. In the interests of brevity, such redundant description of these elements may be omitted.

The data reporting circuitry 210 includes hardware configured to implement data reporting functionality by the apparatus 200. This data reporting functionality may be implemented via a processing element, such as the processor 202, executing one or more algorithms to implement a reporting framework that is operable to transmit system data to a server. The data reporting circuitry 210 may also be configured to receive and execute one or more monitoring scripts or applications for the purpose of gathering and reporting system data.

The system data monitoring circuitry 212 includes hardware for gathering system data, such as a processor (e.g., the processor 202) programmed by a monitoring script or application. As noted above, the system data monitoring circuitry 212 may interact with various hardware and operating system components of the apparatus 200 to gather such system data. This system data may be provided to the data reporting circuitry 210 for transmission to a server, such as the apparatus 100 described above. For example, the system data monitoring circuitry 212 may include hardware and software components configured to determine performance characteristics of the apparatus 200 (e.g., processor and memory usage, network bandwidth utilization, processor temperature, or the like), configuration settings of the apparatus 200 (e.g., display screen resolution, attached input devices, font settings, or the like), and other device status information as reported by device hardware or operating system constructs (e.g., executing processes, device name, operating system version, or the like).

The clinical application circuitry 214 includes hardware for executing one or more clinical applications in furtherance of a clinical task or tasks. The clinical application circuitry 214 includes a processing element, such as the processor 202, which is configured to execute processing functions related to the clinical application or applications.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Example of Data Flow for Implementing System for Improving Clinical Performance

Figure 3:
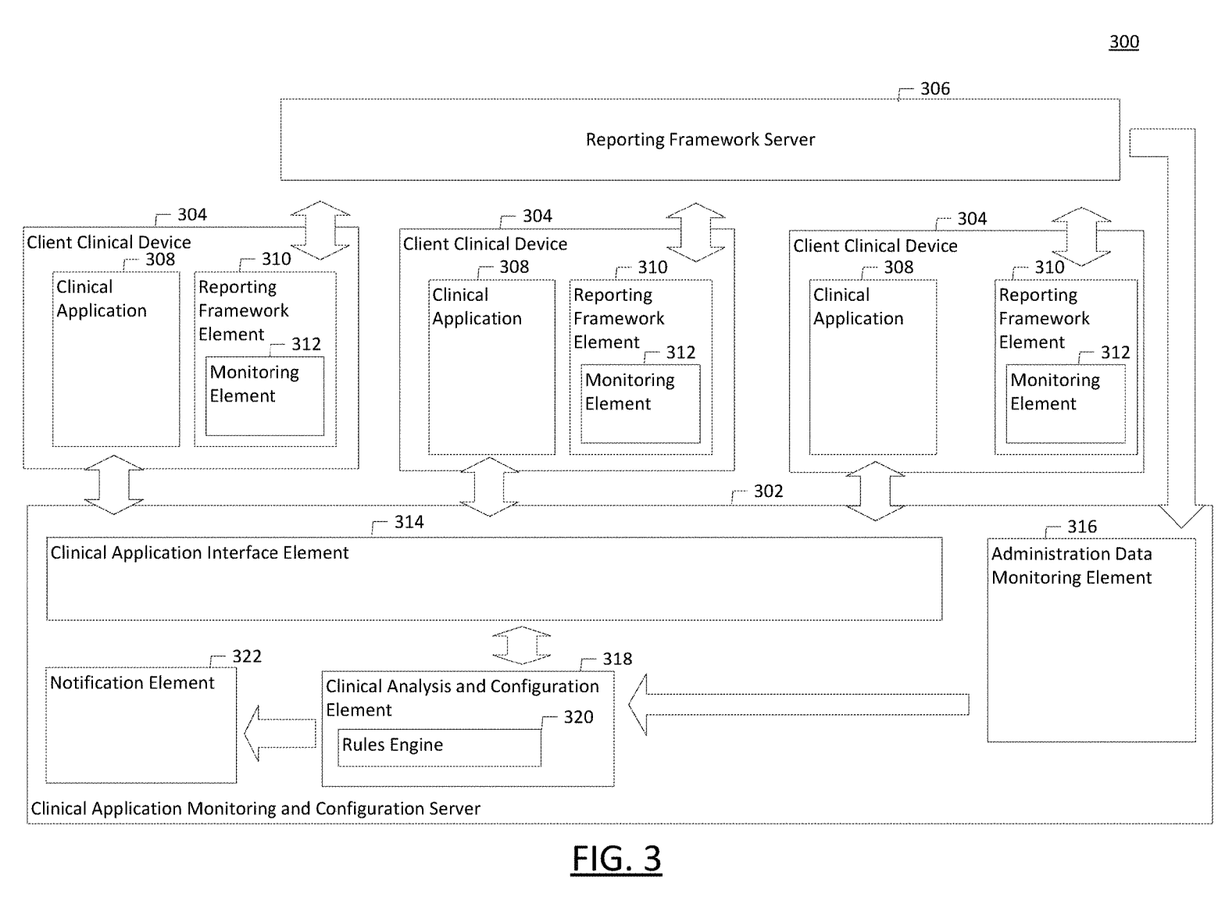
FIG. 3 depicts a data flow among networked devices implementing a system for monitoring client clinical devices in accordance with some embodiments of the present invention.

FIG. 3 illustrates a data flow 300 describing exemplary system interactions for providing improved performance of clinical applications in accordance with embodiments of the present invention. The data flow 300 illustrates interactions among client clinical devices 304 and a clinical application monitoring and analysis server 302 to implement a system for reporting clinical and system data and taking actions based on an analysis of that data as described herein.

Each of the client clinical devices 304 includes a clinical application 308, a reporting framework element 310, and a monitoring element 312. The clinical application 308 may be any application as described above for providing functionality related to a clinical workflow. The clinical application 308 may communicate with the clinical application monitoring and analysis server 302 to provide clinical data for use by the clinical application monitoring and analysis server 302.

The reporting framework element 310 may include an application or software configured to enable data gathering and reporting functionality for reporting data to a reporting framework server 306. The reporting framework element 310 may function to provide an execution environment for the monitoring element 312. For example, the reporting framework element 310 may include an application or the like that is operable to receive scripts, applications, or the like from the reporting framework server 306 and execute those scripts or applications locally to obtain data about the client clinical device, such as system data. The reporting framework element 310 may receive a set of instructions or scripts that indicate which statuses, attributes, performance characteristics, environment variables, registry settings, or the like are to be monitored and reported to the reporting framework server 306. These instructions may be implemented as the monitoring element 312. Although the monitoring element 312 is depicted as executing within the reporting framework element 310, it should be understood that in some embodiments the monitoring element 312 may execute externally to the reporting framework element 312 as a separate process, executable, operating system script, or the like.

The reporting framework server 306 may be a separate computing device from the client clinical device 304 and the clinical application monitoring and configuration server 302, or it may be implemented as a component of one of the client clinical devices 304 or the clinical application monitoring and configuration server 302. The reporting framework server 306 is operable to receive data reported by the reporting framework element 310, including but not necessarily limited to the system data. For example, the reporting framework server 306 may receive the system data and other types of data reported by the reporting framework element 310 and other applications, devices, or systems that utilize the reporting framework implemented by the reporting framework server 306. The reporting framework server 306 may aggregate and transmit the system data to the clinical application monitoring and configuration server 302.

The clinical application monitoring and configuration server 302 includes a clinical application interface element 314, a system data monitoring element 316, a clinical analysis and configuration element 318, and a notification element 322. The clinical application interface element 314 is operable to receive clinical data from the clinical applications 308 and to transmit instructions for configuring those clinical applications to the clinical applications 308. For example, the clinical application interface element 314 may generate one or more network messages or the like to be transmitted to clinical applications executing on the client clinical devices 304. Clinical data received via the clinical application interface element 314 is provided to the clinical analysis and configuration element 318, and instructions for configuring the clinical applications are received from the clinical analysis and configuration element 318.

The system data monitoring element 316 is operable to receive system data from the reporting framework server 306. The received system data is provided to the clinical analysis and configuration element 318. In this regard, the system data monitoring element 316 may be operable to receive a variety of different types of system data. For example, the system data monitoring element 316 may monitor data related to: a server or database configuration (e.g., a number of rows in a data table, a number of current queries with execution times greater than a threshold, or the like), server status data (e.g., when an application pool is down, when a library or other object is not enabled, whether a particular response header is present, or the like), or domain controller data (e.g., a presence of a particular domain user, whether the system is missing proper permissions for a user, an absence of a specific group policy, or the like.

The system data gathered by the system data monitoring element 316 may be provided in a variety of different forms, including but not limited to markup language files (e.g., extensible markup language (XML) files), text files, images, audio files, key-value pairs, comma separated value files, or the like. In some embodiments, this data may be normalized by a reporting framework for reporting such data and formatted into a format suitable for consumption by status analysis circuitry as described above with respect to FIG. 1.

The clinical analysis and configuration element 318 is a processing component that is operable to receive clinical data and system data and identify particular scenarios that may impact the ability of client clinical devices to implement certain clinical functionality. For example, the clinical analysis and configuration element 318 may alter routing behavior of medical images in response to detection that certain performance thresholds are exceeded, launch an alternative viewer application if a first viewer application has exited with an error state, detect a fault in a client clinical device used for routing HL7 messages and configure a device to use an alternative routing device, or the like. As another example, the clinical analysis and configuration element 318 may monitor a status of a viewer applications and the system performance of computing nodes executing those viewer applications. In response to detecting a failure of the viewer application based on the system data, the clinical analysis and configuration element 318 may launch another viewer, alter another viewer to be used as a default viewing application on a different client clinical device, or the like. As yet another example, the clinical analysis and configuration element 318 may notify a clinician in response to detecting that a PACS interface server has failed and that studies may be delayed, and that the clinicians should monitor the PACS directly instead of via the interface server. As another example of a notification process implemented by the clinical analysis and configuration element 318, embodiments may generate a notification to clinicians in response to determining that a cellular network has failed and clinicians should verify information in person. The clinical analysis and configuration element 318 may also be used to implement and alter communication processes, such as by selecting text message or email messages based on a failure of the other communication mechanism.

The clinical analysis and configuration element 318 may implement a rules engine 320 to determine which configuration changes should be made to particular client clinical devices based on particular received clinical and system data. For example, the rules engine may implement a set of comparison operators (e.g., greater than, less than, equal to, contains, does not contain) that enable the creation of if/then statements and other conditionals that cause certain instructions to be transmitted to certain client clinical devices in response to the detection of certain conditions.

In response to meeting the criteria for a particular rule, the rules engine 320 may cause the clinical analysis and configuration element 318 to perform certain tasks. For example, as noted above, these tasks may include informing one or more client clinical devices to alter a configuration setting of a clinical application or otherwise change their configuration. In other scenarios, the tasks may include generating a notification to alert a user or external system that a particular set of circumstances have occurred. For example, some embodiments may generate tasks based on detection of certain system conditions (e.g., a clinical application failing may generate a task for an administrator to restart the application or diagnose the source of the problem), and these tasks may be displayed via a task dashboard implemented by a notification element 322. In other scenarios, communications may be generated and transmitted, such as by creating an email, text message, or the like to transmit the notification to an administrator. The notification element 322, therefore, is configured to implement these features.

Figure 4:
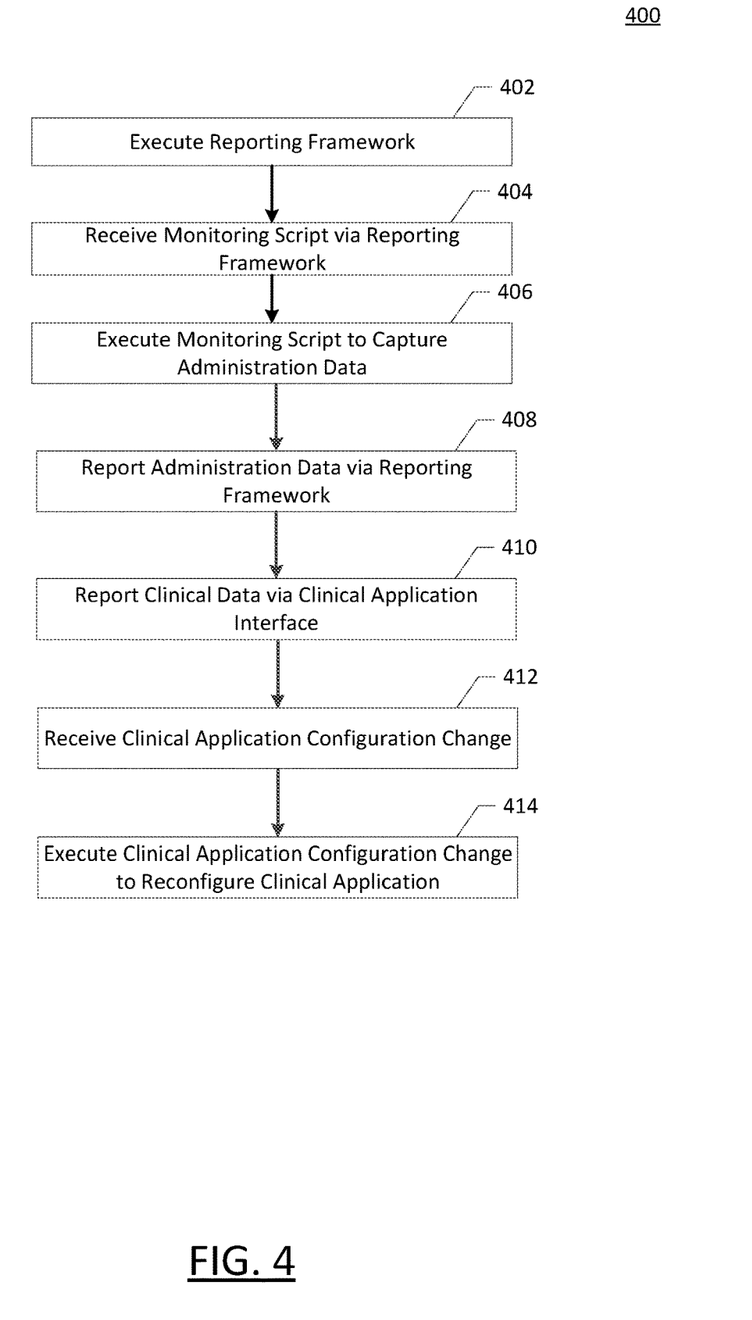
FIG. 4 depicts an illustration of a flow diagram illustrating an example of an algorithm for providing monitoring of client device system data in accordance with some embodiments of the present invention.

Exemplary Processes for Implementing a Clinical Client Monitoring and Configuration System FIG. 4 is a flow diagram depicting an exemplary process 400 as performed by a client clinical device, such as the apparatus 200, for implementing a clinical client monitoring and configuration system in accordance with embodiments of the present invention. The process 400 illustrates a mechanism by which a client clinical device may receive a set of instructions for obtaining and reporting system data, transmit the system data to an external server, and receive configuration settings for a clinical application executing on the client clinical device. In this regard, the process 400 illustrates an example of an algorithm that is implemented via hardware or software executing on hardware components of an apparatus to implement these tasks and other tasks related to client implementation of a clinical client monitoring and configuration system. This algorithm may serve as means for implementing these tasks and other functions as described above and herein.

At action 402, a reporting framework application may be executed. As described above, the reporting framework application may include a software process or application that provides an environment for receiving executable instructions or scripts and executing those instructions or scripts on the client device. For example, the reporting framework application may include a listener thread or process that communicates with a remote server to receive instructions, scripts, or the like.

At action 404, a monitoring script, set of executable instructions, or the like is received, such as from a reporting framework server. At action 406, the monitoring script or set of executable instructions are executed to begin monitoring, capture, and storage of system data regarding the client clinical device. At action 408, the captured system data is transmitted to a clinical application monitoring and configuration server as described above with respect to FIGS. 1 and 3. As described above, reporting of the system data may occur via a reporting framework, such as by transmitting the system data to an intermediate reporting framework server, and the intermediate reporting framework server may in turn relay the system data, along with system data from other client clinical devices, to the clinical application monitoring and configuration server.

At action 410, clinical data may also be captured and reported. This clinical data may also be transmitted to the clinical application monitoring and configuration server. In some embodiments, this transmission may also utilize the reporting framework, while in other embodiments the clinical data may be transmitted directly to the clinical application monitoring and configuration server or through the use of other intermediaries.

At action 412, a configuration change for the clinical application is received from the clinical application monitoring and configuration server. As noted above, this configuration change may result from an analysis of system data and clinical data provided to the clinical application monitoring and configuration server as described above with respect to FIGS. 1 and 3. The configuration change may result from the system data provided by the client device that receives the configuration change, or the configuration change may occur as a result of system data received relating to another client clinical device. At action 414, the configuration change is implemented.

Figure 5:
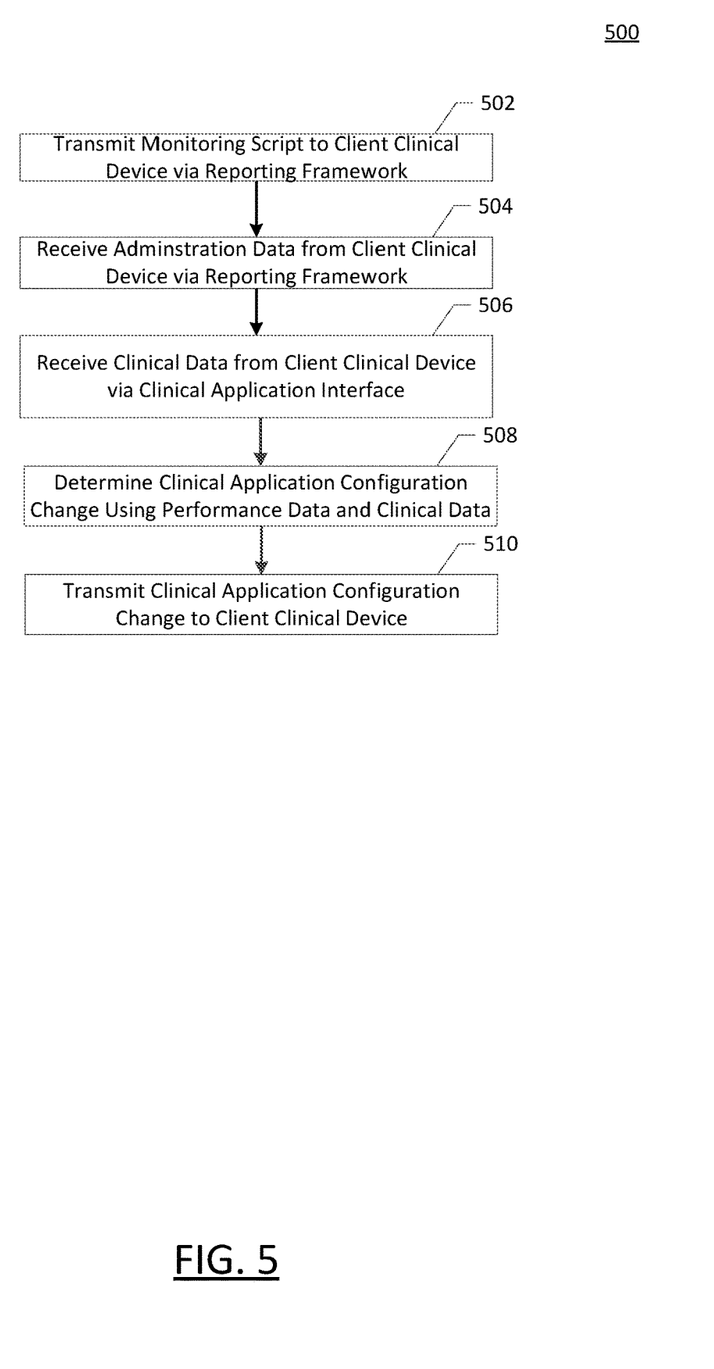
FIG. 5 depicts an illustration of a flow diagram illustrating an example of an algorithm for receiving monitored system data and clinical data from one or more client devices and taking action to implement improved management of client clinical devices in accordance with some embodiments of the present invention.

FIG. 5 depicts a flow diagram illustrating a process 500 for analyzing system data to implement a clinical application configuration change in accordance with some embodiments of the present invention. The process 500 is implemented by a computing device, such as the apparatus 100 described above with respect to FIG. 1, to receive system data, and to generate one or more configuration setting changes to clinical applications to alter one or more clinical workflows in response to the system data meeting certain rule criteria. In this regard, the process 500 illustrates an example of an algorithm that is implemented via hardware or software executing on hardware components of an apparatus to implement these tasks and other tasks related to client implementation of a clinical client monitoring and configuration system. This algorithm may serve as means for implementing these tasks and other functions as described above and herein.

At action 502, a monitoring script or other instructions to begin monitoring operations is transmitted to a client clinical device. As described above, transmission of this script or instructions may be performed via a framework specifically designed to enable the reporting of analytic data, using an executable component of the framework executing on the client clinical device.

At action 504, system data is received from the client clinical device, via the monitoring script or other instructions as executed by the client clinical device. The system data may be reported via the same reporting framework used to transmit the instructions or monitoring script to the client clinical device.

At action 506, clinical data may also be received from the client clinical device. As noted above, the clinical data may be provided directly from a clinical application without the use of the reporting framework, though in some embodiments the reporting framework may also be used to receive the clinical data.

At action 508, the process identifies at least one configuration change for at least one application based on the received system data and/or clinical data. The configuration change may not necessarily occur on a client clinical device that sent the data that prompted the change. For example, a first client clinical device may indicate that system resources are low, and in response a load balancer may be reconfigured to route HL7 message traffic of medical study view operations to a different client clinical device. The determination of the configuration change or other activity to be performed may be made by comparing the system and/or clinical data to a set of rules using a rules engine as described above. In some embodiments, the configuration change may be an output to a task list or dashboard for status monitoring. In such cases, the configuration change may result in a user interface update rather than a direct change to a clinical application.

As a particular example of a configuration change that may be implemented according to a rule set, consider a scenario where the system data indicates that a viewer application has failed on a first clinical device (e.g., the viewer application is no longer listed in a set of running processes). The failure of the viewer application may be relayed to the rules engine using a framework as described herein. In response, the rules engine may cause configuration changes to client clinical devices to route active studies from the failed viewer application to a backup viewer, change the launch configuration on client devices using the failed viewer to instead launch the backup viewer, send a notification to users attempting to access the failed viewer, and send a notification to an administrative user.

As another particular example, the rules engine may determine from the system data that an email server has failed. In response, the rules engine may alert clinical users that certain results and other communication tasks that use email notifications are not working and notifications will be sent using pop-up messages and text messages. The rules engine also configures notification systems on other client clinical devices that use email to use such pop-up messages and text messages instead. The rules engine may also notify a site administrator and revert these configuration changes once the email server is detected as running again, At action 510, the configuration change is transmitted to the associated client clinical device for implementation. As described above, example configuration changes include restarting a service (e.g., a HL7 service) that is detected as failing, moving images to a vendor neutral archive (VNA) and triggering image deletion in response to determining that a PACS server has low disk space, creating a temporary domain controller user account with restricted privileges if the domain controller user account is required by a clinical application or component but the domain controller user account is unavailable.

It will be understood that each element of the flowcharts, and combinations of elements in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 104 or 204 of an apparatus employing an embodiment of the present invention and executed by a processor 102 or 202 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for implementing a clinical client monitoring and configuration system, the method comprising:
    receiving system data from a plurality of client clinical devices, each of the plurality of client clinical devices implementing a reporting framework for transmission of the system data, wherein the system data comprises performance characteristics including one or more of processor utilization, memory utilization, available storage, processor operating temperature or network bandwidth utilization;
    determining, based on the system data, at least one clinical client application configuration change for a clinical application executing on at least one of the plurality of client clinical devices or another client clinical device other than the plurality of client clinical devices;
    transmitting instructions to the clinical application for implementation of the at least one clinical client application configuration change; and
    transmitting at least one of a script or executable instructions to the plurality of client clinical devices via the reporting framework, such that execution of the script or executable instructions causes a client clinical device receiving the script or executable instructions to monitor at least one of statuses, attributes, performance characteristics, environment variables, or registry settings and to transmit a report of the at least one of statuses, attributes, performance characteristics, environment variables, or registry settings.

2. The method of claim 1, wherein the system data comprises performance data for one or more of the plurality of client clinical devices.

3. The method of claim 1, wherein determining the configuration change comprises:
    determining, from the system data, that a first viewer application has failed; and
    routing at least one imaging study from the first viewer application to a second viewer application.

4. The method of claim 3, further comprising configuring at least one launch configuration file of at least one of the plurality of client clinical devices to use the second viewer application to view the imaging study instead of the first viewer application.

5. The method of claim 1, further comprising receiving clinical data from the clinical application, wherein the configuration change is determined based in further part on the clinical data.

6. The method of claim 1, wherein the plurality of client clinical devices comprise at least one of a Picture Archiving and Communications System, an electronic health records system, a Health Level 7 (HL7) server, or an admission, discharge, transfer system.

7. An apparatus for implementing a clinical client monitoring and configuration system, the apparatus comprising a processor and a memory, the memory storing instructions that are executed by the processor to configure the processor to at least:
    receive system data from a plurality of client clinical devices, each of the plurality of client clinical devices implementing a reporting framework for transmission of the system data, wherein the system data comprises performance characteristics including one or more of processor utilization, memory utilization, available storage, processor operating temperature, or network bandwidth utilization;
    determine, based on the system data, at least one clinical client application configuration change for a clinical application executing on at least one of the plurality of client clinical devices or another client clinical device other than the plurality of client clinical devices;

transmit instructions to the clinical application for implementation of the at least one clinical client application configuration change; and transmit at least one of a script or executable instructions to the plurality of client clinical devices via the reporting framework, such that execution of the script or executable instructions causes a client clinical device receiving the script or executable instructions to monitor at least one of statuses, attributes, performance characteristics, environment variables, or registry settings and to transmit a report of the at least one of statuses, attributes, performance characteristics, environment variables, or registry settings.

8. The apparatus of claim 7, wherein the system data comprises performance data for one or more of the plurality of client clinical devices.

9. The apparatus of claim 7, wherein determining the configuration change comprises:
   determining, from the system data, that a first viewer application has failed; and
   routing at least one imaging study from the first viewer application to a second viewer application.

10. The apparatus of claim 9, wherein the apparatus is further configured to configure at least one launch configuration file of at least one of the plurality of client clinical devices to use the second viewer application to view the imaging study instead of the first viewer application.

11. The apparatus of claim 7, further configured to receive clinical data from the clinical application, wherein the configuration change is determined based in further part on the clinical data.

12. The apparatus of claim 7, wherein the plurality of client clinical devices comprise at least one of a Picture Archiving and Communications System, an electronic health records system, a Health Level 7 (HL7) server, or an admission, discharge, transfer system.

13. A non-transitory computer readable storage medium comprising program instructions that, when executed by a processor, configure the processor to at least:
   receive system data from a plurality of client clinical devices, each of the plurality of client clinical devices implementing a reporting framework for transmission of the system data, wherein the system data comprises performance characteristics including one or more of processor utilization, memory utilization, available storage, processor operating temperature, or network bandwidth utilization;

determine, based on the system data, at least one clinical client application configuration change for a clinical application executing on at least one of the plurality of client clinical devices or another client clinical device other than the plurality of client clinical devices;

transmit instructions to the clinical application for implementation of the at least one clinical client application configuration change; and transmit at least one of a script or executable instructions to the plurality of client clinical devices via the reporting framework, such that execution of the script or executable instructions causes a client clinical device receiving the script or executable instructions to monitor at least one of statuses, attributes, performance characteristics, environment variables, or registry settings and to transmit a report of the at least one of statuses, attributes, performance characteristics, environment variables, or registry settings.

14. The computer readable storage medium of claim 13, wherein the system data comprises performance data for one or more of the plurality of client clinical devices.

15. The computer readable storage medium of claim 13, wherein determining the configuration change comprises:
   determining, from the system data, that a first viewer application has failed; and
   routing at least one imaging study from the first viewer application to a second viewer application.

16. The computer readable storage medium of claim 15, wherein the instructions further configure the processor to configure at least one launch configuration file of at least one of the plurality of client clinical devices to use the second viewer application to view the imaging study instead of the first viewer application.

17. The computer readable storage medium of claim 13, wherein the instructions further configure the processor to receive clinical data from the clinical application, wherein the configuration change is determined based in further part on the clinical data.

* * * * *